United States Patent [19]

Fortier

[11] Patent Number: 5,733,563
[45] Date of Patent: Mar. 31, 1998

[54] ALBUMIN BASED HYDROGEL

[75] Inventor: Guy Fortier, Montreal, Canada

[73] Assignee: Universite du Quebec a Montreal, Canada

[21] Appl. No.: 591,941

[22] Filed: Jan. 23, 1996

Related U.S. Application Data

[63] Continuation of Ser. No. 159,559, Dec. 1, 1993, abandoned.

[51] Int. Cl.$^6$ .............................. A61F 13/00; A61F 2/00
[52] U.S. Cl. .................. 424/422; 424/423; 424/424; 424/425; 424/427; 424/429; 424/445; 424/434
[58] Field of Search ........................... 424/422, 423, 424/424, 425, 427, 429, 445, 434

[56] References Cited

U.S. PATENT DOCUMENTS

| | | | |
|---|---|---|---|
| Re. 33,997 | 7/1992 | Kuzma et al. | 523/106 |
| 3,463,862 | 8/1969 | Mazza | 523/106 |
| 4,101,380 | 7/1978 | Rubinstein et al. | 195/63 |
| 4,161,948 | 7/1979 | Bichon | 128/156 |
| 4,264,155 | 4/1981 | Miyata | 351/160 H |
| 4,388,428 | 6/1983 | Kuzma et al. | 523/106 |
| 4,464,468 | 8/1984 | Avrameas et al. | 435/177 |
| 4,650,616 | 3/1987 | Wajs | 264/2.6 |
| 4,752,627 | 6/1988 | Froix | 526/106 |
| 4,879,072 | 11/1989 | Bourset et al. | 264/1.4 |
| 5,039,540 | 8/1991 | Ecanow | 426/385 |
| 5,051,406 | 9/1991 | Satoh | 514/21 |
| 5,079,018 | 1/1992 | Ecanow | 426/385 |
| 5,114,627 | 5/1992 | Civerchia | 264/1.1 |

*Primary Examiner*—Nathan M. Nutter
*Attorney, Agent, or Firm*—Cushman Darby & Cushman IP Group of Pillsbury Madison & Sutro LLP

[57] ABSTRACT

Novel bioartificial hydrogels consisting of a three-dimensional crosslinked mixture of: (a) a bifunctionalized polyethylene oxide, activated with an activating agent, dissolved in an aqueous solution; and (b) albumin type protein. The novel hydrogels are based on the crosslinking of albumin type protein of various sources including, for example, bovine serum albumin, lactalbumin or ovalbumin, with a bifunctionalyzed polyethylene oxide, most preferably polyethylene glycol, or a mixture of bifunctionalyzed polyethylene oxides preferably polyethylene glycol, of various molecular masses (Mr 2,000 to 35,000), dissolved in aqueous solution in adequate proportions. Also provided is a method and conditions for preparing the novel hydrogels. Also divulged are a variety of biomedical applications for the novel hydrogels. Additionally, it has been found that the mechanical properties of the novel hydrogels can be improved by adding to the casting solution unreactive polyethylen glycol or other inert polymer of high molecular masses (Mr>100,000). In general terms the novel hydrogels possess advantageous properties such as shape retention and shape memory, high water content (more than 94% (w/w) based on the dry weight of the hydrogel), good mechanical and optical properties.

16 Claims, 6 Drawing Sheets

FIGURE 1

Effect of the molecular masses of PEG on the gelling time of BSA-PEG hydrogel in two different buffer pHs (filled dots, 0.1M borate buffer pH: 9.4 and open dots, 0.1M borate buffer pH: 8.8

FIGURE 2

Effect of PEG/$NH_2$ ratio on the gel formation. The bars represent the minimum and the maximum at which gel formation occurs.

FIGURE 4

FIGURE 5 Slow controlled release of theophylline in PBS at room temperature from hydrogels prepared with BSA and PEG of various molecular masses

FIGURE 6

Operational stability of acid phosphatase immobilized in BSA-PEG, Mr 10,000, in presence of 10 mM of p-nitrophenylphosphate (flow rate of 1,25 ml/min).

ALBUMIN BASED HYDROGEL

This is a continuation of application Ser. No. 08/159,559, filed on Dec. 1, 1993, which was abandoned on the filing hereof of application Ser. No. 08/591,941, filed on Jan. 23, 1996.

FIELD OF THE INVENTION

This invention relates to the preparation of high water content bioartificial hydrogels obtained from the cross-linking of albumin type proteins, such as bovine serum albumin (hereinafter referred to as BSA) with bifunctionalyzed polyethylene glycol, or other suitable bifunctionalyzed polyethylene oxide, of various molecular masses, in different proportions, in an aqueous solution.

BACKGROUND OF THE INVENTION

The term "hydrogel" refers to a class of polymeric materials which are extensively swollen in a aqueous medium, but which do not dissolve in water. In general terms, hydrogels are prepared by polymerization of a hydrophylic monomer under conditions where the polymer becomes cross-linked in a three dimensional matrix sufficient to gel the solution. Bioartificial or semi-synthetic hydrogels may also be prepared by the covalent addition of the hydrophylic polymer to the surface of a protein so that the polymer and protein form a further covalently cross-linked three dimensional matrix. This class of hydrogels made from a synthetic polymer and a biopolymer has been recently reviewed and it has been proposed to name this new class of biomaterials as bioartificial polymeric material or hydrogel (Giusti, P et al, *Trends in Polymeric Science*, (:261–267, 1993).

The usefulness and multiplicity of desirable applications of hydrogels in medicine and other areas as well as their composition and methods of their preparation have been well documented. For example, in a two volume book series, *Hydrogels in medicine and pharmacy*, vol. 1 & 2, N. A. Peppas ed. CRC Press publ., USA, 1986; or other books such as *Polymer in Medicine*, R. M. Ottenbrite and E. Chiellini, Technomic publ., USA, 1992, as well as several scientific publications such as: *The design of hydrogel for biomedical applications*, by P. H. Corkhill, C. J. Hamilton and B. J. Tighe in *Crit. Rev. Biocompatibility*, 5: 363–435, 1990; Bioartificial Polymeric Materials: a new method to design biomaterials by using both biological and synthetic polymers, P. Giustic, L. Lasseri and L. Lelli, *Trends in Polymeric Science*, 9: 261–267, 1993.

Some of the more notable biomedical applications of hydrogels include contact lenses, non-toxic in-vivo controlled drug release implants, wound dressings, cell growth matrices. Novel or improved hydrogels having improved properties, applications or ease of preparation are of course required.

The present invention concerns a novel bioartificial hydrogel prepared from the cross-linking of a polyethylene oxide, or derivative thereof, preferably polyethylene glycol (hereinafter arbitrarily referred to in its abbreviated form as PEG), with albumin type protein.

With the benefit of the above described background of hydrogels, the known prior art will now be addressed.

PRIOR ART

With regards to bioartificial hydrogels, methods for the covalent addition of hydrophylic polymers such as monomethoxy-polyethylene glycol (hereinafter referred to as mPEG) to the surface of a protein have been successfully developed using a variety of reagents (review in *Biotechnol. Appl. Biochem.* 17: 115, 1993; *TIBECH*, 4: 190, 1986 & 6: 131, 1988). mPEG has generated a great deal of interest when it was first used to modify the surface of proteins and enzymes in the aim of reducing their immunogenicity and to increase their blood clearance time for potential in vivo applications (*J. Biol. Chem*, 252: 3578, 1977 and 252: 3582, 1977). Such soluble modified proteins or enzymes have shown an increase in their structural resistance against proteolytic action of proteases (*J. Ferment. Bioeng.*, 71: 137–139, 1991), an increase of their rate of adsorption by the gastro-intestinal tractus (*Biol. Chem. Hoppe Seyler* 101: 3715, 1990) and an increase of their cellular influx (*Proc. Natl. Acad. Sci. USA*, 84: 1487, 1987). Such modified enzymes have also shown a good activity as microparticulate suspensions in organic solvents (*Enzyme Microb. Technol.*, 14: 96–100, 1992; *TIBECH*, 4: 190, 1986 & 6: 131, 1988). mPEG can even be used as a blood substitute when covalently bound to the protein heamoglobin (*J. Prot. Chem.* 10: 61–67, 1991). When the surface of a material is covered by mPEG, the protein adsorption on this surface is reduced (2nd *Congress on Biomaterials*, USA 1984) as well as the complement activation and the platelet adhesion (*Biomaterials*, 13: 113–118, 1992).

Recently, the preparation of a gel using a mixture of copolymerized acrylic derivatives of chymotrypsin and polyethylene oxide acrylate derivatives has been described in the literature (*Int. J. Peptide Protein Res.* 38: 273–277, 1991). The gel was utilized successfully in organic solvents for peptide synthesis. However, the authors do not offer any mention regarding the characterization of the protein aggregates obtained using this procedure. The protanous gel cannot be considered as an hydrogel since the reactions were performed in an organic medium as opposed to an aqueous medium.

A detailed review on the chemistry of polyethylene glycol and its biotechnological and biomedical applications is found in (*Polyethylene glycol chemistry, Biotechnological and biomedical applications*, Milton Harris ed. Plenum Press, 1992) as well as the book entitled *Hydrogels in medicine and pharmacy*, ed. by N. A. Peppas, especially the chapter 4 of Volume 2 which focuses on poly(ethylene oxide) and related hydrogels. Many PEG based hydrogels are therein described without any mention of cross-linking of PEG with a protein. It is demonstrated that PEG can be considered as an useful polymer and hydrogel by itself for many biomedical uses because of its specific and advantageous properties: it is a non thrombogenic material, it presents a low toxicity, it is approved by FDA (Food & Drug Agency) as polymer in foodstuffs and pharmaceutical products used via injection, topical or oral routes. When PEG was converted into a cross-linked network (an hydrogel), it passed regulatory requirements. One of the most popular polymer for hydrogel synthesis was for some time the polyHEMA which unfortunately suffered biocompatibility problems which ultimately restricted its usage.

Presently the majority of hydrogels are prepared from a mixture of polymer or block copolymer cross-linked by radiation or chemical reagent or simply prepared by polymerization and reticulation of a monomeric solution. One important drawback arising from these methods are the inherent difficulties in achieving reproducibility in specific porosity and degree of cross-linking which ultimately affect many characteristics of the resulting hydrogel. Control of the chain length of the polymer used, the hydrophylicity, and the molecular masses of the copolymer (cross-linker) along with controlled mild aqueous reaction conditions, are the key to success in achieving reproducibility, size pore control, water swelling control, and geometry control of the hydrogel.

U.S. Pat. No. 4,101,380, the specification of which is incorporated herein by reference, discloses a very wide variety of reagents useful to activate polyethylene oxide in the aim of obtaining a bifunctionalyzed polyethylene oxide or polyalkene oxide. When those reagents are used to cross-link PEG with a gelatin preformed membrane, a cross-linked gelatin-PEG membrane was obtained and was characterized by an high liquid swelling capacity. However, other embodiments described in the patent provided very low yield of protein cross-linking (in the order of of about 2%). In said patent, there is no mention or suggest that advantageous hydrogels could be obtained by cross-linking of an albumin or an other native protein in an aqueous solution with activated polyethylene oxide. Moreover, said patent states that the use of a carbonate derivative of polyethylene oxide is not recommended and not useful should attempts be made to obtain cross-linking of the polymer with a protein or enzyme. This is explained as being due to the high pH required for the subsequent cross-linking reaction which could induce denaturation of enzymes or proteins.

The present invention demonstrates in sharp contrast that the use of a carbonate polyethylene oxide derivative should be very useful for the preparation of cast hydrogels having reproducible specific geometries as required, for example, when making contact lenses or devices for controlled drug release. Although the pH of reaction is higher than 9 during cross-linking with a protein or enzyme, the present invention confirms that PEG carbonate derivatives are useful reagents for enzyme or protein modifications which prevent denaturation of many enzymes (catalase, peroxidase, superoxide dismutase, acid phosphatase, glucose oxidase, lysozyme, and asparaginase).

U.S. Pat. No. 4,161,948 discloses synthetic membranes (artificial skin) for wound dressings. Said patent suggests that when preparing the membranes, it is preferable that the δ-amino acid polymers employed be cross-linked with a diol such as polyoxyethylene glycol, in order to achieve properties resembling those of natural human collagen. Polypeptides as a source of polyamino functional groups were not mentioned in said patent. According to said patent, δ-amino acid polymers are prepared by a polymerisation process which results in a statistically distributed polymer in a wide range of molecular weights. The fabrication of the artificial skin described in said patent is obtained via a complex multi step process. It is obvious, from the disclosure of said patent, that the inventors, are experiencing great difficulty in controlling the porosity and the cross-linking of the synthetic membrane and are resorting to a complex method.

U.S. Pat. No. 4,752,627 discloses a contact lens which contains polymerized ethylene glycol moieties as side chains to the major polymer (HEMA, polyvinyl pyrrolidone) components. Said patent explains that the use of PEG as a side chain component contributes to the ability of the lens to resist to the absorption of proteins present in human tears. Depending on the amount of the hydrophobic cross-linker used to prepare the hydrogel, an equilibrium water content varying from 18 to 60% was obtained. Such a degree of water swelling is unfortunately not sufficient to allow free diffusion of oxygen similar to the corresponding rate in a solution.

U.S. Pat. No. 4,814,182 discloses the preparation of a controlled release device based on a hydrogel coated with an impermeable layer on at least one side of the device. The hydrogel was obtained from the polymerization of block copolymers comprising both hydrophylic and hydrophobic domains, preferably polyethylene oxide methacrylate which reacted with a substituted or unsubstituted cyclic mono or polyether having from 3 to 6 ring atoms or cyclic imine. The use of a protein as a polyamino groups source is not mentioned in said patent.

U.S. Pat. No. Reissue 33,997 discloses a contact lens based on the cross-linking of collagen with an ethylenically unsaturated compound of varying length from one to six carbons. The hydrogel described therein displayed good biological stability to protease digestion and protein fouling (adsorption).

SUMMARY OF THE INVENTION

Unexpectedly, a family of novel hydrogels has been discovered. The novel hydrogels are polymerized hydrophylic water-swellable gels essentially consisting of a cross-linked mixture of: (a) a bifunctionalized polyethylene oxide, activated with a suitable activating agent, dissolved in an aqueous solution; and (b) albumin type protein albumin. The novel hydrogels are based on the cross-linking of a protein, namely albumin of various sources including, for example, BSA, with a bifunctionalyzed polyalkene oxide preferentially polyethylene oxide, and most preferably polyethylene glycol, or a mixture of bifunctionalyzed polyalkene oxides of various molecular masses (Mr 2,000 to 35,000) dissolved in aqueous .solution, in adequate proportions.

The present invention also provides a method and conditions for preparing the novel hydrogels.

A variety of biomedical applications for the novel hydrogels are also envisaged and method for preparing the products related to those applications are claimed. Additionally, it has been found that the mechanical properties of the novel hydrogels can be improved by adding to the casting solution unreactive PEG or other inert polymers of high molecular masses (Mr>100,000).

Accordingly, the novel hydrogels possess many advantageous properties such as shape retention and shape memory, they can reach very high water content (more than 94% (w/w) based on the dry weight of the hydrogel). The novel hydrogels also possess good mechanical and optical properties. The hydrogels further possess more characteristics which may render them extremely useful in the pharmaceutic and medical areas due to their advantageous properties such as biocompatibility, resistance to proteases action, slow release of various drugs, hydrophylic surface, good oxygen permeability, controlled porosity, and other desirable properties.

These and other objectives can be achieved by practising the teachings disclosed herein. It is to be noted that specific examples relating to the possible applications of the novel hydrogels will be described and do not represent an exhaustive enumeration and consequently do not limit all other possible applications of the novel hydrogels which are to be contemplated and understood.

BRIEF DESCRIPTION OF THE DRAWINGS

These and other advantages of this invention will be readily apparent when considered in light of the following description when considered in light of the drawing set forth with comprises the following figures.

DESCRIPTION OF THE PREFERRED EMBODIMENTS

The invention relates to novel hydrogels, their preparation, and applications. The novel hydrogels can, for example and without necessary or implied limitations, be used for making contact lenses, controlled drug release devices, immobilisation matrix for enzymes or cells of therapeutic interest as enzyme correction, wound dressing and artificial skin.

In a preferred embodiment, the hydrogels generally contain a significant amount of polyethylene glycol cross-linked with a protein, namely albumin from various sources such as bovine serum (BSA), (M.W., 67,000), egg (M.W., 43,000) or milk (M.W., 14,400). The polyethylene glycol is activated to form water soluble polyethylene oxide derivatives of the general formula 1:

wherein X can be any type of functionalized groups able to react with an amino, a S—H, an OH or a COOH group brought by a protein, and n can vary from 45 to 800 which corresponds to commercial PEG of Mr ranging from 2,000 to 35,000.

The activation of polyethylene glycol by a reagent such as 4-nitrophenyl chloroformate is known to be possible by various methods described in patents and other scientific literature (U.S. Pat. No. 4,101,380, *Biotech. Appl. Biochem*, 17: 115, 1993; *Polyethylene glycol Chemistry: Biotechnical and Biomedical applications*, ed J. M. Harris, chap 21, pp. 347–370, Plenum Press, N.Y. 1992), which are incorporated herein by reference.

EXPERIMENTAL

Activation of PEG

In accordance with a preferred embodiment, the activation of PEG to obtain a reagent able to react with amino groups will now be briefly described.

Polyethylene glycol of various molecular masses (n varying from 45 to 800) were activated using 4-nitrophenyl chloroformate in order to obtain a series of PEG dinitrophenyl carbonates (*Biotech. Appl. Biochem*, 17: 115, 1993). The method will now be narrated in more detail. Before use, all PEGs had been dehydrated by dissolving 1.0 mmole of a PEG in acetonitrile and refluxing at 80° C. for 4 hours in a Soxhlet (trade-mark) extractor containing 2.0 g of anhydrous sodium sulfate. The dehydrated solution containing 1.0 mmole of PEG was activated in the presence of at least 3.0 mmoles of 4-nitrophenyl chloroformate in acetonitrile containing up to 5 mmoles of triethylamine. The reaction mixture was heated at 60° C. for 5 hours. The reaction mixture was cooled and filtered and the synthesized PEG-dinitrophenyl carbonate was precipitated by the addition of ethyl ether at 4° C. The percentage of activation was evaluated by following the release of p-nitrophenol from the activated PEG in 0.1M borate buffer solution, pH 8.5, at 25° C. The hydrolysis reaction was monitored at 400 nm until a constant absorbance was obtained. The purity was calculated based on the ratio of the amount of p-nitrophenol released and detected spectrophotometrically versus the amount of p-nitrophenol expected to be released per weight of activated PEG used for the experiment. The purity of the final products was found to be around 90%.

Preparation of the hydrogel of albumin cross-linked with PEG.

Covalent cross-linking of the activated PEG to albumin of various sources, for example serum (BSA), milk (lactalbumin) or egg (ovalbumin), was obtained by adding to one ml of 5% (w/v) protein solution (in either phosphate or borate buffer) different amounts of the activated PEG (from 7 to 13% w/v), followed by vigourous mixing until all the PEG powder was dissolved. The cross-linking reaction was performed at pH 8.8 except for PEG molecular masses inferior to 5000 for which a more basic buffer (pH 9.3) was used. The ratio of reagents (PEG/NH2 free groups of protein) was determined taking into account that bovine serum albumin (BSA) has 27 accessible free NH2 groups. The hydrogel obtained was incubated in 50 mM borate buffer pH 9.8 in order to hydrolyse the unreacted PEG-dinitrophenyl carbonate. The released p-nitrophenol, the unlinked PEG, and the free BSA were eliminated from the gel matrix by washing the hydrogel in distilled water containing NaN$_3$ 0.02% for many hours.

In these experimental conditions, the rate of polymerization was found to be a function of the pH of the reaction. When the reaction was performed at pH 7.8, the time required for gel formation is 1000 min contrary to what was observed at pH 10.3 where the gelification is obtained in less than 5 minutes.

Figure 1:
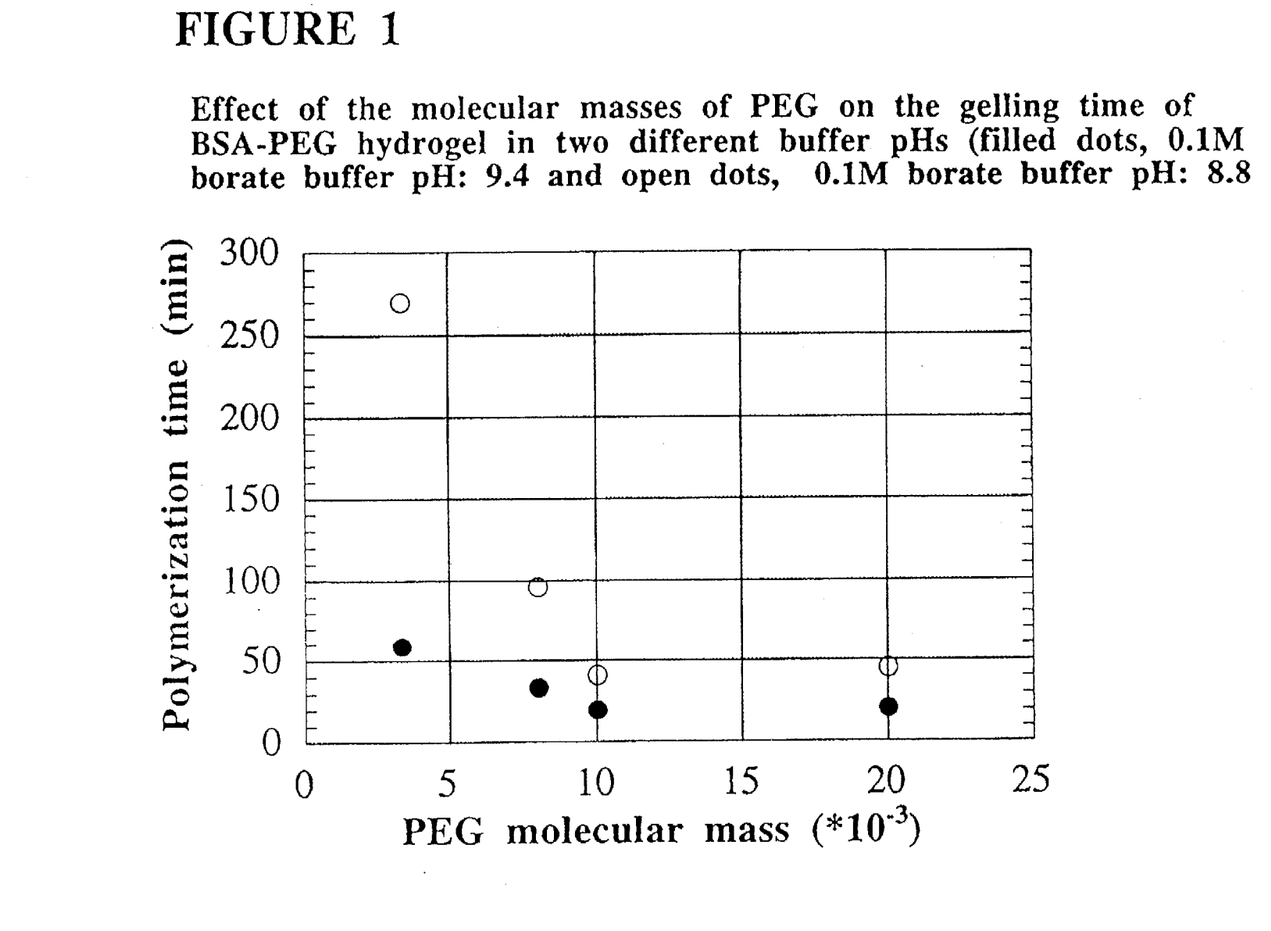
FIG. 1 is a graphical representation of the effect of the molecular masses of PEG (horizontal scale) on the gelling time (vertical scale) of a BSA-PEG hydrogel in two different buffer pH solutions (the filled dots indicate a 0.1M borate buffer of pH 9.4 and the open dots indicate a 0.1M borate buffer of pH 8.8).

Referring now to FIG. 1, it is shown that at an intermediary pH of reaction values, intermediary reaction times were obtained.

Figure 2:
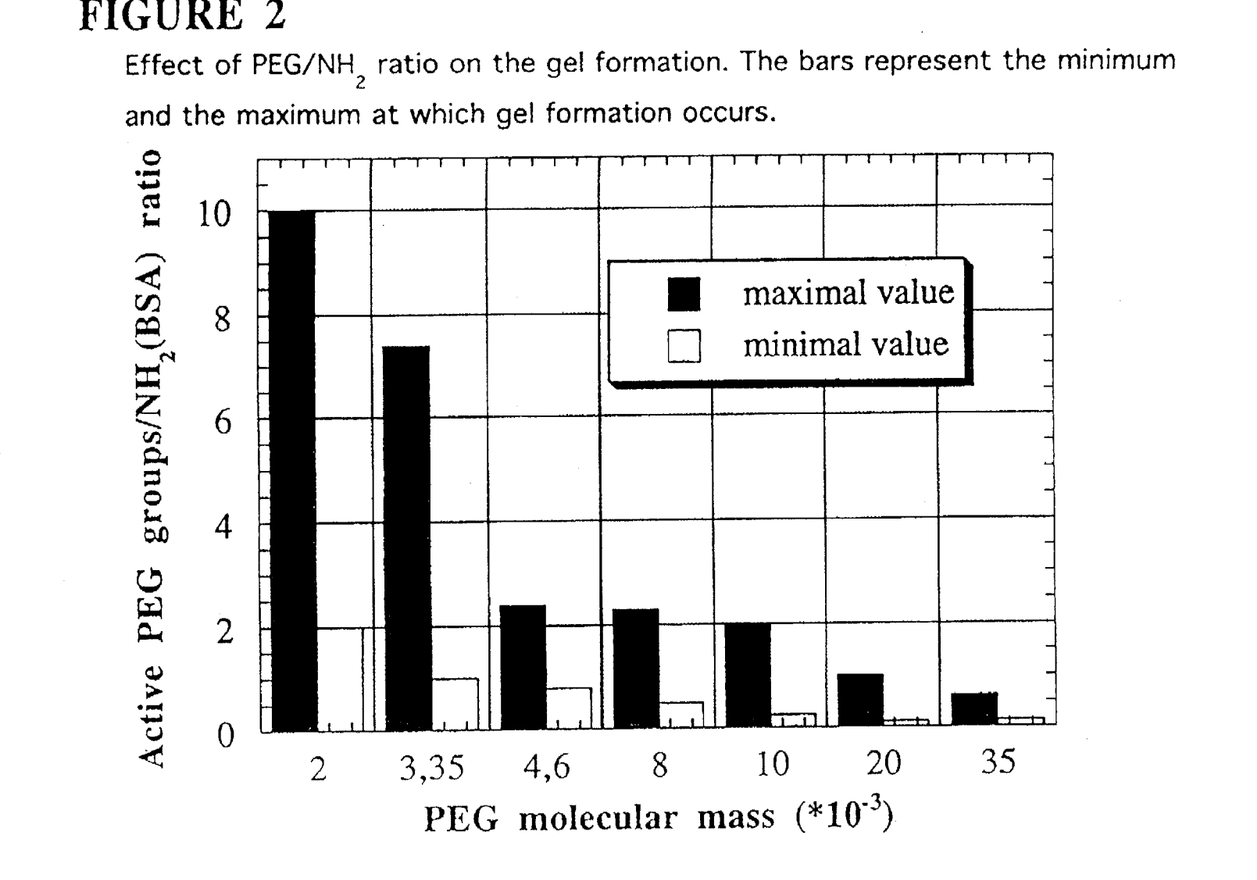
FIG. 2 is a graphical representation of the effect of the PEG/NH$_2$ ratio (vertical scale) on gel formation with regards to PEG molecular mass (horizontal scale) with dark bars representing maximal values and light bars representing minimal values.

Referring now to FIG. 2, the PEG/NH$_2$ ratio (defined as the molar ratio of PEG activated groups versus albumin accessible NH$_2$ group) leading to the formation of a solid hydrogel ranged from 0.12 to 10 depending of the molecular masses of PEG used. The optimum ratio was found to corresponds to the ratio where the release of albumin and PEG are at a minimum during the washing steps. In general terms, the higher the Mr of PEG used, the smaller is the average ratio PEG/NH$_2$ needed to obtain a solid hydrogel, see FIG. 2. The decrease of the ratio is tought to be partially explained by an increase of steric hindrance when high molecular masses of PEG are used.

Evaluation of the degree of swelling of the hydrogel.

After completion of washing (until a colourless gel is obtained, which corresponds in this case to the elimination of any residual trace of p-nitrophenol), the hydrogels were dehydrated under vacuum or by acetone washes. In order to evaluate the effects of pH and of the ionic strength on the water uptake of the hydrogel, the dry PEG-albumin gels were weighed and incubated in various buffer solutions (acetate, phosphate or borate buffers) at various levels of pH and molarities. The swelling of the dry hydrogel was periodically evaluated by measuring the increase of gel volume in a graduated cylinder or by weighing. The swelling solution was changed once during the procedure. The swelling factor (SF) is calculated from equation 2 which is adapted from the work on the polyvinyl alcohol hydrogels (Urushisaki et al., *Int J. Pharm.*, 58: 135, 1990):

$$\text{swelling factor} = (Ws - Wth)/Wth \quad (2)$$

were Ws is the final weight after swelling and Wth is the dry weight measured at the end of experiment by drying the hydrogel at 70° C. until complete dehydration. The swelling capacity of an hydrogel can also be described by an equilibrium water content value (EWC) which is defined in equation 3:

$$EWC = (\text{weight of water/weight of the swollen hydrogel}) \times 100 \quad (3)$$

The swelling kinetics in a PBS solution at pH 7.3 at 20° C., were evaluated for hydrogels prepared using PEG of Mr of 10,000 (PEG/$NH_2$ molar ratio of 1.3) and PEG of Mr of 20,000 (PEG/$NH_2$ molar ratio of 0.5). For the hydrogels obtained with PEG 10,000 or PEG 20,000, a steady state in the swelling kinetic was observed after 100 and 80 hours, respectively. A linear velocity of the water uptake as a function of the square root of the time was observed during the first 8 hours for both hydrogels. For all the hydrogels (Mr from 3,350 to 20,000) the EWCs obtained in distilled water containing 0.02% of sodium azide showed a swelling EWC of 96.5 to 98%. In the absence of sodium azide, the EWC of every hydrogel became greater than 99%, a value at which the hydrogels obviously became fragile and their manipulation difficult.

Another series of swelling experiments was performed with different hydrogels made from various ratio of PEG/$NH_2$ in 50 mM borate buffer. The SF observed ranged from 14 to 21 with a maximum value observed for an hydrogel obtained with a PEG of Mr 10,000 (PEG/$NH_2$ molar ratio of 0.4). More details are provided in Table I below.

TABLE I

Evaluation of the swelling parameters (Swelling Factor and of the Equilibrium water content) of different hydrogels obtained using bovine serum albumin and various molecular masses of PEG, at the optimum (PEG/$NH_2$) ratio.

| Mr of PEG | Ratio PEG-OH/$NH_2$ | Swelling Factor[1] X | Equilibrium water content[1] % |
|---|---|---|---|
| 3,350 | 3.0 | 13.9 | 93.3 |
| 4,600 | 1.6 | 14.1 | 93.4 |
| 8,000 | 1.4 | 20.5 | 95.3 |
| 10,000 | 1.2 | 20.9 | 95.4 |
| 20,000 | 0.4 | 19.3 | 95.1 |

[1] These parameters were obtained by incubating the various hydrogels in 50 mM borate buffer pH 8.8 containing 0.02% sodium azide. In absence of azide and buffer, the equilibrium water content reached a value greater than 99%. At these values, all hydrogels are too fragile to be manipulated and breaked easely.

Permeability of the hydrogel to oxygen

In a study on dissolved oxygen permeability for a range of hydrogels, Ng and Tighe found the log of permeability coefficient to be linearly related to the overall EWC (*Br. Polym. J.*, 8: 78, 1976; 8: 118, 1976). This relation was later confirmed by Refojo and Leong, (*J. Membran. Sci.*, 4: 415, 1979). Using this relation along permeability data available in the literature, and considering an EWC at least greater than 94% at 20° C. in an isotonic solution, the oxygen permeability of the hydrogels of the present invention is projected to approach the value of oxygen diffusion in a water solution (Corkhill et al, *Crit. Rev. Biocompatibility* 5: 363, 1990).

Translucidity of the various hydrogels.

Figure 3:
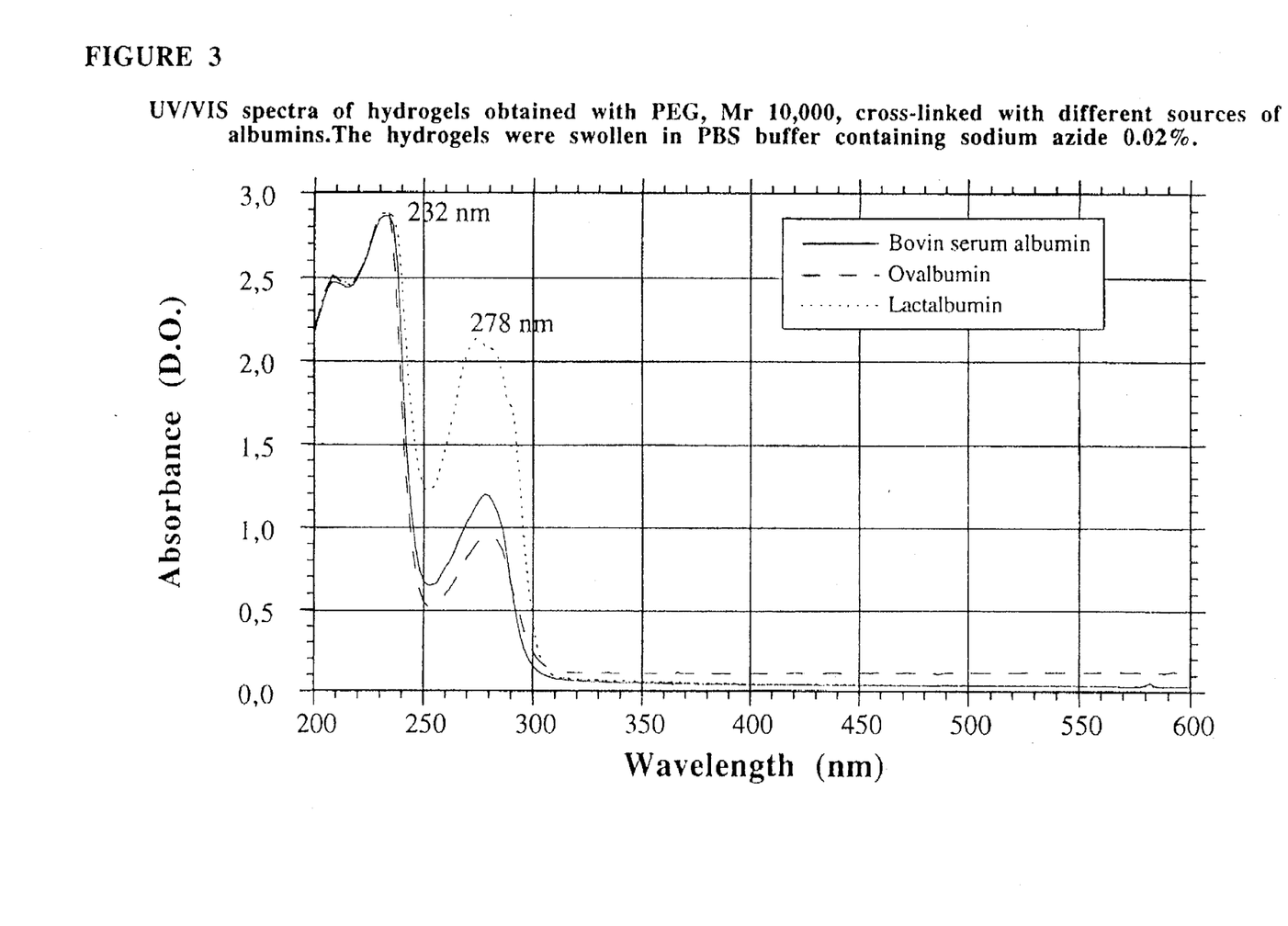
FIG. 3 is a graphical representation of absorbance (vertical scale) versus wavelength (horizontal scale) for hydrogels obtained with PEG, Mr 10,000, cross-linked with different sources of albumins. For UV spectra analysis, the hydrogels were swollen in PBS buffer containing sodium azide 0.02%.

As shown in FIG. 3, the absorption spectra of three different types of hydrogels of the present invention, obtained with PEG, Mr 10,000 and cross-linked to bovine serum albumin, lactalbumin or ovalbumin did not display any peak absorption for wavelengths greater than 340 nm (corresponding to the visible region of light spectrum). Due to their high transmittance in the visible region of the light spectrum, these hydrogels can be considered as a good material to elaborate contact lenses or ophthalmologic devices as well as wound covering devices (in this later case, the wound dressing transparency could allow the degree of healing to be visualized). The spectra given in FIG. 3 were obtained using an Hewlett-Packard diode array spectrophotometer for PEG Mr 10,000 hydrogels previously swollen in a phosphate buffer salts solution (PBS) containing sodium azide at 0.02% and placed directly in a custom made gel holder.

Evaluation of the rheologic properties of the new family of hydrogels

The rheologic properties of the hydrogels were evaluated using an Instron 4201 (trade-mark) instrument at room temperature. The viscoelasticity characteristics for hydrogels prepared with PEGs of Mr 3,350 and 20,000, respectively, swollen in 100 mM phosphate buffer, were established from their curves of gel deformation versus time at constant compression (0.5 cm/min) applied until the hydrogel collapsed. Up to 70% of compression, the hydrogel obtained using PEG of molecular masse of 20,000 and BSA exhibited a perfect or near perfect elastic behaviour and the gel breaking force was found to be 8 N/$cm^2$ (no correction of force was given to relate the increase of the contact surface with the increase of compression). With hydrogels obtained using PEG of Mr 3,350, the break of the gel appeared at 50% of compression and required a force of 10.6N/$cm^2$. Based on these preliminary studies, a trend was observed between the increase of the molecular masses of PEG and the increase of the elasticity of the hydrogel.

FURTHER DESCRIPTION OF APPLICATIONS AND POTENTIAL USES OF THE HYDROGELS OF THE PRESENT INVENTION

Applications and potential uses of this new family of hydrogels in wet form include: 1) contact lens or other ophalthalmic device; 2) slow drug released device such as capsule, cutaneous patch or implant; 3) matrix for immobilization of cells or enzymes for in vivo, in vitro or ex vivo use as a bioreactor or biosensor; 4) artificial skin; and 5) wound dressing.

A dry form of these hydrogels (obtained after dehydration under vacuum or in acetone) can also be used first as water or exudate absorbent in wound dressing, second as a slow or controlled drug release devices.

Some of these potential applications will now be discussed in the following examples which are to be construed as illustrative as opposed to limitative.

EXPERIMENTAL

Slow or controlled drug release device.

A thin film (3 mm thick) of hydrogel made from PEG of molecular masses of 10,000 and BSA, was cut into pastilles of 0.8 to 1.8 cm in diameter and used as a slow drug released devices. The pastille were loaded and allowed to swell overnight at room temperature in a solution containing the drug (250 µg/ml in phosphate buffer salts solution (PBS) in which 20%/vol of ethanol was added to dissolve the steroids). The pastilles were then fixed onto a microscope glass slab and its circumference coated with white petroleum jelly in order to have only one releasing surface. The pastilles were incubated in PBS and the release of the drug from the pastilles was monitored in a closed circulatory device connected to a spectrophotometer. The drug release was monitored at the wavelength where the absorption of the drug was maximal, during more than ten hours. The release kinetics were analyzed to fit equation (4) (P. L. Ritger and N. A. Peppas, *J. Controlled release*, 8: 37, 1987), which can be used to analyze the part of the curve corresponding to $M_t/M_\infty < 0.60$:

$$M_t/M_\infty = k\, t^n \quad (4)$$

where $M_t$ and $M_\infty$ are the amount of drug released at t and infinite time, k is a rate constant of the release and n is a value representing the mechanism of the release. For n=0.5, the drug is released following a Fickian mechanism.

Figure 4:
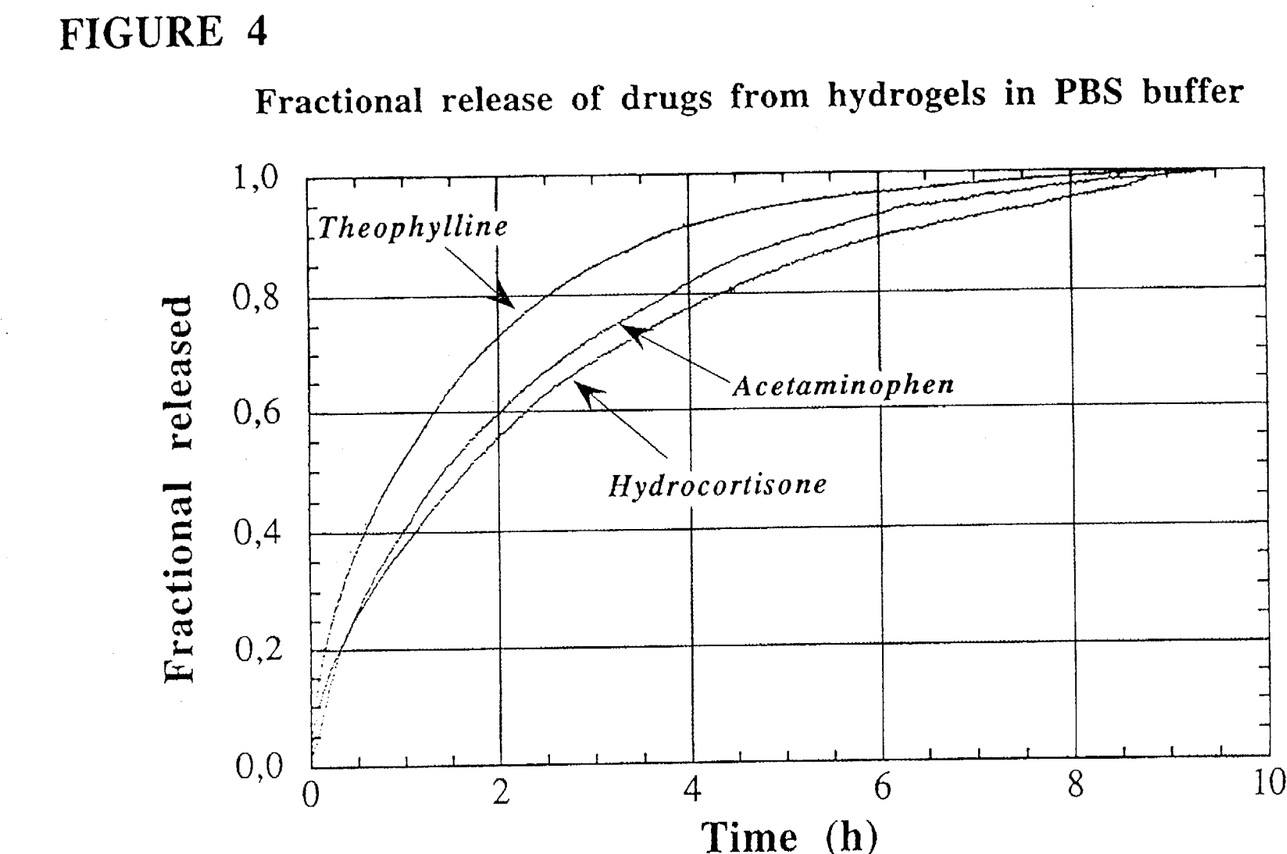
FIG. 4 shows the fractional release (vertical scale) of three example drugs over time (horizontal scale).

Referring now to FIG. 4, the release patterns of three common drugs, namely theophylline, acetaminophen and hydrocortisone from hydrogels (active surface: 1.1 cm$^2$, thickness 3 mm) prepared with BSA and PEG, Mr 10,000, are given. Table 2 below provides the value of the exponent n along with the coefficient of correlation when equation 4 is used to fit the curves. The compounds studied are acetaminophen, cortisone, hydrocortisone, lysozyme, methylene blue, prednisone, tetracycline and theophylline.

TABLE 2

Compilation of the values of the exponent n (eq 4) along with the coefficient of correlation of the fit, and the diffusion coefficient (eq. 5), assuming n = 0.5, for the compounds listed. Pastilles of BSA-PEG 10,000 (ratio was 1.1) were loaded in triplicata by immersion for 24 hours in solution containing 250 µg/ml of the different compounds (see text). The release study was carried out in 30 ml of PBS at room temperature.

| Drug | Exponent n | r | D (cm$^2$/s) |
| --- | --- | --- | --- |
| Theophylline | 0.511 | 0.999 | $14.7 \cdot 10^{-7}$ |
| Acetaminophen | 0.596 | 0.998 | $10.7 \cdot 10^{-7}$ |
| Tetracycline | 0.522 | 0.999 | $10.1 \cdot 10^{-7}$ |
| Cortisone | 0.569 | 0.999 | $8.6 \cdot 10^{-7}$ |
| Hydrocortisone | 0.562 | 0.999 | $8.6 \cdot 10^{-7}$ |
| Prednisone | 0.557 | 0.999 | $8.3 \cdot 10^{-7}$ |
| Methylene blue | 0.520 | 0.999 | $8.3 \cdot 10^{-7}$ |
| Lysozyme | 0.520 | 0.999 | $1.26 \cdot 10^{-7}$ |

For each compound shown in table 2, the value of the exponent n is very close to 0.5, which is indicative of a Fickian release process. The coefficient of diffusion, D, given in table 2 was calculated using equation (5) (R. Baker, *Controlled Release of Biologically Active Agents*, John Wiley and Sons Inc., NY, p.51, 1987):

$$M_t/M_\infty = 4(Dt/\pi l^2)^{0.5} \quad (5)$$

where D is the coefficient of diffusion, l is the slab thickness, other symbols representing the same variables as those described above for equation (4). An hydrogel of high water content in which the diffusion of a compound follows the Fick law, is very convenient because the half-life of the release is controlled by the geometry of the hydrogel such as the slab thickness.

Figure 5:
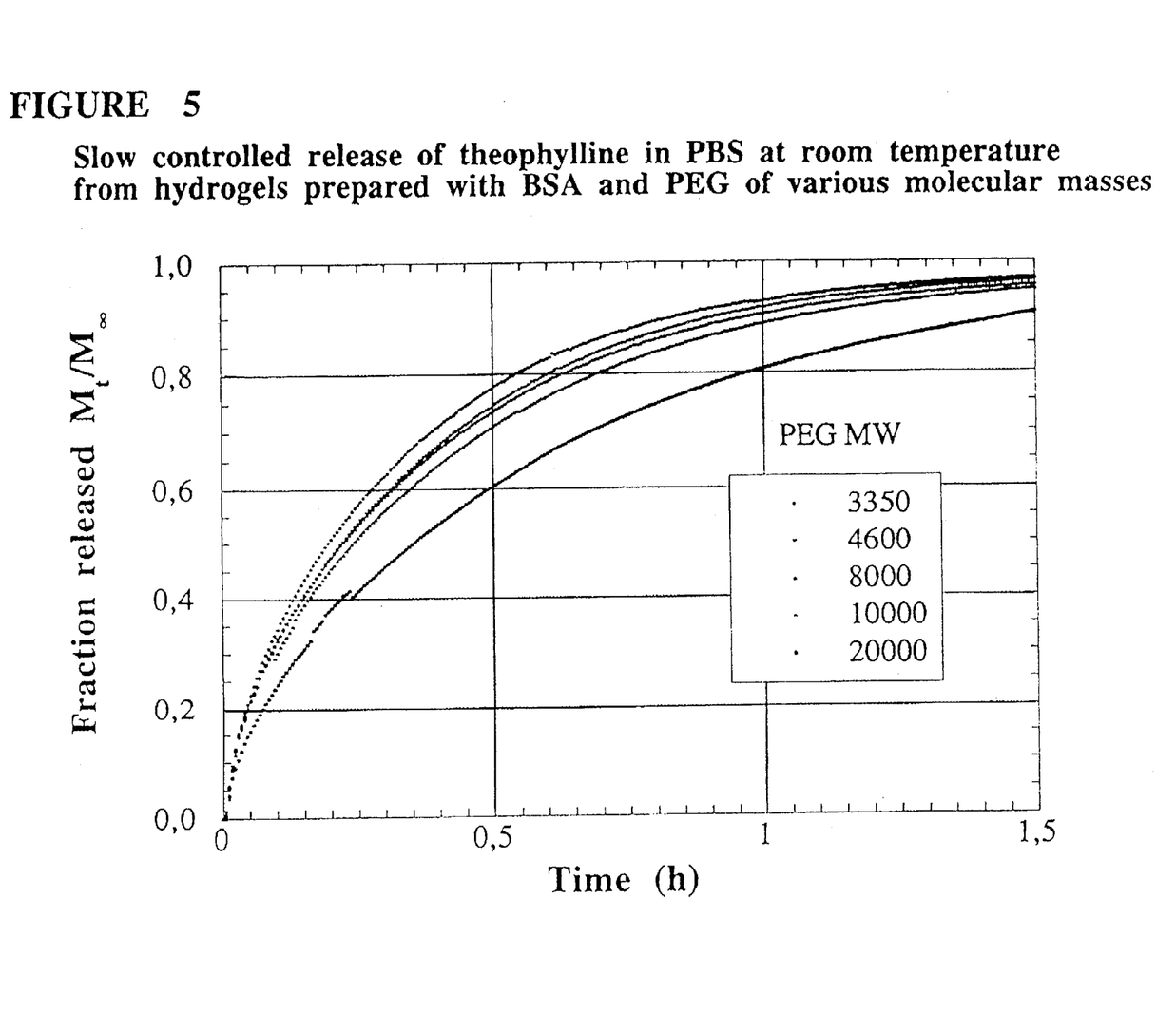
FIG. 5 shows the fractional release (vertical scale) of theophylline as an example drug over time (horizontal scale) for hydrogels of the present invention prepared with BSA and PEG of various molecular masses.

Referring now to FIG. 5 there is described the theophylline release from hydrogels (active surface: 0.8 to 1.8 cm$^2$, thickness 1 mm) prepared with BSA and PEG of various molecular masses. The calculated exponent n and coefficients of diffusion of the related preparations are compiled in Table 3.

TABLE 3

Compilation of the values of the exponent n (eq 4) along with the coefficient of correlation of the fit, and the diffusion coefficient (eq. 5), assuming a value of n = 0.5, for the theophylline loaded in pastilles of BSA-PEG prepared with the various molecular masses indicated below. The various pastilles were loaded in triplicata by immersion in solution containing 250 µg/ml of theophylline for 24 hours. The release study was carried out in 30 ml of PBS at room temperature.

| PEG | (ratio) | Exponent n | r | D (cm$^2$/s) |
| --- | --- | --- | --- | --- |
| 3350 | (3:1) | 0.564 | 0.998 | $12.6 \cdot 10^{-7}$ |
| 4600 | (1.6:1) | 0.570 | 0.997 | $13.4 \cdot 10^{-7}$ |
| 8000 | (1.4:1) | 0.533 | 0.997 | $15.4 \cdot 10^{-7}$ |
| 10000 | (1.3:1) | 0.556 | 0.998 | $16.1 \cdot 10^{-7}$ |
| 20000 | (0.6:1) | 0.568 | 0.998 | $17.1 \cdot 10^{-7}$ |

It can be concluded that for a wet hydrogel, the release of drug from the hydrogel approaches a Fickian mechanism (n=0.5). Other experiences (results not shown herein) have demonstrated that the release time for a given compound is proportional to the thickness of the pastilles. Also, the coefficient of diffusion, calculated assuming n=0.5, was found to increase with the decrease of the molecular masses of PEG.

It is to be understood that the present slow or controlled release composition may also contain excipients, such as binders, disintegrating agents, colours, flavours, preservatives, stabilisers, glidants and lubricants, the use of which will be well known to those skilled in the pharmaceutical art. Any therapeutically effective amount of active ingredient that may be loaded into the hydrogel of the present invention can be employed. Experimental examples of some compounds have been specifically given above. However, with the proviso that they do not substantially alter the cross-linking structure of the hydrogels and that preferably the drugs are water-soluble, further examples of active ingredients that may advantageously be incorporated in the present composition are:

| DRUG | pH |
| --- | --- |
| Acetazolamide, Sodium | 9.0–10.0 |
| Alphaprodine HCl | 4.0–6.0 |
| Amicocaproic Acid | 6.0–7.6 |
| Aminosuppurate Sodium | 6.7–7.6 |
| Aminophylline | 8.6–9.0 |
| Aminotryptyline HCl | 4.0–6.0 |
| Amobarbitol Sodium | 9.6–10.4 |
| Anileridine | 2.5–3.0 |
| Amphotericin B | 7.2–8.0 |
| Ampicillin | 5.0–7.0 |
| Anti coagulant Heparin Solution | 5.0–7.0 |
| Arginine HCl | 5.0–6.5 |
| Atropine Sulfate | 3.0–6.5 |
| Atrial Peptides | |
| Azathioprine Sodium | 9.8–11.0 |
| Benztropine Mesylate | 5.0–8.0 |
| Betaine HCl | 0.80–1.2 |
| Betamathazone Sodium | 8.0 |

-continued

| DRUG | pH |
|---|---|
| Bethanecol Chloride | 5.5–7.5 |
| Biperiden Lactate | 4.8–5.8 |
| Bleomycin Sulfate | 4.5–6.0 |
| Brompheniramine Maleate | 5.8–7.0 |
| Bupivacaine-Epinephrine Injection | 3.3–8.5 |
| Bupivacaine HCl | 4.0–6.5 |
| Butabartitol Sodium | 10.0–11.2 |
| Butorphanol Tartrate | 3.0–5.5 |
| Caffeine-Soidum Benzoate Injection | 6.5–8.5 |
| Calcium Glueptate Injection | 5.6–7.0 |
| Calcium Levulinate | 6.0–8.0 |
| Carboprost Tromethiamine Injection | 7.0–8.0 |
| Cefamandole Sodium | 6.0–8.5 |
| Cefamandole Nafate | 6.0–8.0 |
| Caphazolin Sodium | 4.5–7.0 |
| Cafataxime Sodium | 4.5–65. |
| Ceftizoxime Sodium | 4.5–6.5 |
| Cephalothin Sodium | 4.5–8.0 |
| Caphaprin Sodium | 6.5–8.0 |
| Caphradine | 8.0–9.6 |
| Cafonocid Sodium | — |
| Chloramphenicol | 5.0–8.0 |
| Chlordiazepoxide HCl | 2.5–3.5 |
| Chloroprocaine HCl | 2.7–4.0 |
| Chlorothiazide Sodium | 9.2–10.0 |
| Chlorpromazine HCl | 3.0–5.0 |
| Cefoperazone Sodium | 4.5–6.5 |
| Chlorphenramine Maleate | 4.0–5.2 |
| Chloroquine HCl | 5.5–6.5 |
| Chlortetracycline NCl | 2.3–3.3 |
| Clorprothixene | 4.0–5.0 |
| Colohicine Desmopressin | 6.0–7.0 |
| Clindamycin Phosphate | 5.5–7.7 |
| Cimetadine Hydrochloride | 4.0–6.0 |
| Codeine Phosphate | 3.0–6.0 |
| Corticotropin | 2.5–6.0 |
| Cyanocobalamin | 4.5–7.0 |
| Cyclizine Lactate | 3.2–4.7 |
| Cyclophosphamide | 3.9–6.7 |
| Cyclosporine | — |
| Cysteine HCl | 1.0–2.5 |
| Chlorprothixene HCl | 3.4 |
| Dantrolene Sodium | 9.5 |
| Dacarbazine | 3.0–4.0 |
| Cactinomycin | 5.5–7.5 |
| Daunorubicin HCl | 4.5–6.5 |
| Deslanoside | 5.5–7.0 |
| Desmopressin Acetate | 3.0–5.0 |
| Dexamethasone Sodium Phosphate | 7.0–8.5 |
| Diatrizoate Meglumine | 6.0–7.7 |
| Diatrizoate Sodium | 4.5–7.5 |
| Diazepam | 6.2–6.9 |
| Diazoxide | 11.2–11.9 |
| Dibucaine HCl | 4.5–7.0 |
| Dicyclomine HCl | 5.0–5.5 |
| Diethylstilbesterol Diphosphate | — |
| Digoxin | — |
| Dihydroergotamine Mesylate | 3.2–4.0 |
| Diphenhydramine HCl | 4.0–6.5 |
| Dimenhydrinate | 6.4–7.2 |
| Dobutamine HCl | 2.5–5.5 |
| Dopamine HCl | 2.5–5.5 |
| Dopamine HCl-Dextrose | 3.0–5.0 |
| Doxapram HCl | 3.5–5.0 |
| Doxorubicin HCl | 3.8–6.5 |
| Droperidol | 3.0–3.8 |
| Dhphylline | 5.0–8.0 |
| Edetate Disodium | 6.5–7.5 |
| Emetine HCl | 3.0–4.0 |
| Ephedrine Sulfate | 4.5–7.0 |
| Epinephrine | 2.5–5.0 |
| Ergonovine Maleate | 2.7–3.5 |
| Ergotamine Tartrate | 3.0–4.0 |
| Erythromycin | — |
| Erythromycin Ethylsuccinate | 6.0–8.5 |
| Erythromycin Gluceptate | 6.0–8.0 |
| Erythromycin Lactibionate | 6.5–7.5 |
| Estradiol Valerate | — |

-continued

| DRUG | pH |
|---|---|
| Ethacrynate Sodium | 6.3–7.7 |
| Ethylnorepinephrine HCl | 2.5–5.0 |
| Etidocaine HCl | 11.0 |
| Fentanyl Citrate | 4.0–7.5 |
| Floxuridine | 4.0–5.5 |
| Fluorescein Sodium | 8.0–9.0 |
| Fluoracil | 8.6–9.0 |
| Fluphenazine Enanthate | — |
| Fluphenazine HCl | 4.8–5.2 |
| Folic Acid | 8.0–11.0 |
| Furosemide | 8.5–9.3 |
| Fallamine Triethiodide | 5.3–7.0 |
| Gentamycin Sulfate | 3.0–5.5 |
| Glucagon | 2.5–3.0 |
| Glycopyrrolate | 2.0–3.0 |
| Haloperidol | 3.0–3.8 |
| Heparin-Calcium | 5.0–7.5 |
| Heparin-Sodium | 5.0–7.5 |
| Hetacillin-Potassium | 7.0–9.0 |
| Hexafluorenium Bromide | 4.0–7.0 |
| Histamine Phosphate | 3.0–6.0 |
| Hyaluranidase | 6.4–7.4 |
| Digitoxin | — |
| Fructose | 3.0–6.0 |
| Hydralazine HCl | 3.4–4.4 |
| Hydrocortisone Sodium Phosphate | 7.5–8.5 |
| Hydrocortisone Sodium Succinate | 7.0–8.0 |
| Hydromorphone HCl | 4.0–5.0 |
| Hydoxocobalamin | 3.5–5.0 |
| Hydroxyzine HCl | 3.5–6.0 |
| Hyoscyamine Sulfate | 3.0–4.5 |
| Imipramine HCl | 4.0–5.0 |
| Iophendylate | 6.5–7.7 |
| Iothalamate Sodium | 6.5–7.7 |
| Iron Dextran | 5.2–6.5 |
| Isobucaine HCl-Epinephrine | — |
| Isoniazid | 6.0–7.0 |
| Isoproterenol HCl | 3.5–4.5 |
| Isoxsuprine HCl | 4.9–6.0 |
| Kanamycin Sulfate | 3.5–5.0 |
| Ketamine HCl | 3.5–4.5 |
| Leucovorin Calcium | 6.5–8.5 |
| Levallorphan Tartrate | 4.0–4.5 |
| Lidocaine HCl | 5.0–7.0 |
| Lidocaine HCl Dextrose | 3.5–7.0 |
| Lidocaine HCl-Epinephrine | 3.3–5.5 |
| Lidocaine HCl-Epinephrine Bitartrate | 3.3–5.5 |
| Lincomycin HCl | 3.0–6.6 |
| Magnesium Sulfate | 5.5–7.0 |
| Magnesium Chloride | 1.5–2.5 |
| Methlorethamine HCl | 3.0–5.0 |
| Menotropins | 6.0–7.0 |
| Meperidine HCl | 3.5–6.0 |
| Mephentermine Sulfate | 4.0–6.5 |
| Mepivacaine HCl | 4.5–6.8 |
| Mepivacaine HCl-Levonordefrin | 3.3–5.5 |
| Meprylcaine HCl-Epinephrine | 3.5–5.5 |
| Mesoridazine Besylate | 4.0–5.0 |
| Metaraminol Bitartrate | 3.2–4.5 |
| Methadone HCl | 3.0–6.5 |
| Methicillin Sodium | 5.0–7.5 |
| Methiodal Sodium | 5.0–8.0 |
| Methocarbamol | 3.5–6.0 |
| Methohexital Sodium | 10.6–11.6 |
| Methotrexate Sodium | 8.0–9.0 |
| Methotrimeprazine | 3.0–5.0 |
| Methoxamine HCl | 3.0–5.0 |
| Methscopolamine Bromide | 4.5–6.0 |
| Methyldopate HCl | 3.0–4.2 |
| Methylergonovine Maleate | 2.7–3.5 |
| Methylpredisolone Sodium Succinate | 7.0–8.0 |
| Metronidazone | 4.5–7.0 |
| Miconazole | 3.7–5.7 |
| Minocycline HCl | 2.0–3.5 |
| Mitomycin | 6.0–8.0 |
| Morphine Sulfate | 2.5–6.0 |
| Moxalactam Disodium | 4.5–7.0 |
| Nafcillin Sodium | 6.0–8.5 |

| DRUG | pH |
|---|---|
| Naloxone HCl | 3.0–4.5 |
| Neostigmine Methylsulfate | 5.–6.5 |
| Netilmicin Sulfate | 3.5–6.0 |
| Niacin | 4.0–6.0 |
| Niacinamide | 5.0–7.0 |
| Norepinephrine Bitartrate | 3.0–4.5 |
| Nylidrin HCl | 4.5–6.5 |
| Orphenadrine Citrate | 5.0–6.0 |
| Oxacillin Sodium | 5.0–8.5 |
| Oxymorphone HCl | 2.7–4.5 |
| Oxytetracycline | 8.0–9.0 |
| Oxytetracycline HCl | 2.0–3.0 |
| Oxytocin | 2.5–4.5 |
| Papaverine HCl | 3.0 or less |
| Parathyroid | 2.5–3.5 |
| Penicillin G Potassium | 6.5–8.5 |
| Penicillin G Procaine | 5.0–7.5 |
| Penicillin G Sodium | 6.5–7.5 |
| Pentazocine Lactate | 4.0–5.0 |
| Phenobarbital Sodium | 9.0–10.5 |
| Perphenazine | 4.2–5.6 |
| Phenobarbital Sodium | 9.0–10.5 |
| Perphenazine | 4.2–5.6 |
| Phenobarbitol Sodium | 9.2–10.2 |
| Phentolamine Mesylate | 4.5–6.5 |
| Phenylephrine HCl | 3.0–6.5 |
| Phenytoin Soidum | 10.0–12.3 |
| Physopstigmine Salicylate | 4.0–6.0 |
| Phytonadione | 3.5–7.0 |
| Plicamycin | 5.0–7.5 |
| Posterior Pituitary | 2.5–4.5 |
| Potassium Acetate | 5.5–8.0 |
| Potassium Chloride | 4.0–8.0 |
| Prednisolone Sodium Phosphate | 7.0–8.0 |
| Prednisolone Sodium Succinate | 5.7–8.0 |
| Prilocaine HCl | 5.0–7.0 |
| Procainamide HCl | 4.0–6.0 |
| Procaine HCl | 3.0–5.5 |
| Procaine HCl-Epinephrine | 3.0–5.5 |
| Procaine-Phsnylephrine Hydrochlorides | 3.0–5.5 |
| Procaine and Tetracaine HCl and Levonodefrin | 3.5–5.0 |
| Prochlorperazine Edisylate | 4.2–6.2 |
| Promazine HCl | 4.0–5.5 |
| Promethazine HCl | 4.0–5.5 |
| Propiomazine HCl | 4.7–5.3 |
| Propoxycaine-Procaine HCl's-Norepinephrine Bitartrate | 3.5–5.0 |
| Propanolol HCl | 2.8–4.0 |
| protein Hydrolysate | 4.0–7.0 |
| Pyridostigmine Bromide | 4.5–5.5 |
| Pyridoxine HCl | 2.0–3.8 |
| Quinidine Gluconate | — |
| Reserpine | 3.0–4.0 |
| Riboflavin | 4.5–7.0 |
| Ritodrine HCl | 4.8–5.5 |
| Rolitetracycline | 3.0–4.5 |
| Scopolamine HCl | 3.5–6.5 |
| Secobarbital Sodium | 9.0–10.5 |
| Sisomycin Sulfate | 2.5–5.5 |
| Spectinomycin HCl | 3.8–5.6 |
| Streptomycin Sulfate | 5.0–8.0 |
| Succinylcholine Chloride | 3.0–4.5 |
| Sulfadixazine Sodium | 8.5–10.5 |
| Sulfixoxazole Diolamine | 7.0–8.5 |
| Superoxide Dismutase | — |
| Terbutaline Sulfate | 3.0–5.0 |
| Testosterone Cypionate | — |
| Testosterone Enanthate | — |
| Tetracaine HCl | 3.2–6.0 |
| Tetracycline HCl | 2.0–3.0 |
| Tetracycline Phosphate Complex | 2.0–3.0 |
| Thiamine HCl | 2.5–4.5 |
| Thimylal Sodium | 10.7–11.5 |
| Thiethylperazine Maleate | 3.0–4.0 |
| Thiopental Sodium | 10.2–11.2 |
| Thiothixene HCl | 2.5–3.5 |
| Tobramycin Sulfate | 6.0–8.0 |
| Tolazoline HCl | 3.0–4.0 |
| Tolbutaminde Sodium | 8.0–9.0 |
| Triamcinolane Diacetate | 6.0 |
| Tridihexethyl Chloride | 5.0–7.0 |
| Trifluoperazine HCl | 4.0–5.0 |
| Triflupromzine HCl | 3.5–52. |
| Trimethaphan Camsylate | 4.9–5.6 |
| Trimethobenzamide HCl | 4.8–5.2 |
| Trimethoprimsulfamethoxazole | 10.0 |
| Tromethamine | 10.0–11.5 |
| Tubocurarine Chloride | 2.5–5.0 |
| Vasopressin | 2.5–4.5 |
| Vincristine Sulfate | 3.5–4.5 |
| Vidarabine Concentrate | 5.0–6.2 |
| Vinclastine Sulfate | 3.5–5.0 |
| Warfarin Sodium | 7.2–8.3 |
| Verapamil | 4.1–6.0 |

Examples of drug in standard dosage forms:

| | |
|---|---|
| Cimetidine HCl | 150 mg/ml |
| Diazepam | 5 mg/ml |
| 5-Fluorouracil | 500 mg/10 ml |
| Erythromycin Lactobionate | 1 mg/ml |
| Flosuridine | 500 mg/5 ml |
| Amthoteracin D | 0.1 mg/ml |
| Fluphenazine HCl | 2.5 mg/ml |
| Heparin Sodium | 1,00–20,000 units/ml |
| Haloperidol lactate | 5 mg/ml |
| Insulin | 40 units |
| Ketamine HCl | 10 mg/ml |
| Labeltol HCl | 5 mg/ml |
| Lipocaine HCl | 10 mg/ml |
| Miconazole | 10 mg/ml |
| Morphine Sulfate | 0.5–1.0 mg/ml |
| Dropendal | 2.5 mg/ml |
| Imipramine HCl | 25 mg/2 ml |
| Phenytoin | 100 mg/ml |
| Pentobartital Sodium | 50 mg/ml |
| Tetracycline HCl | 250 mg/100 ml |
| Thiopental Sodium | 0.2 mg/2 ml |
| Verapamil HCl | 2.5 mg/ml |
| Vincristine Sulfate | 1.0 mg/ml |
| Fentanyl citrate | 0.05 mg/ml |
| Methylprednisolone Sodium Succinate | 40 mg/ml |

It is to be understood that the above list of drugs is for the purpose of illustration only and is not provided as an all inclusive list of the drugs which may be beneficially incorporated in the slow or controlled release composition of the present invention.

Matrix for enzyme immobilisation.

In a first step, the albumin type protein was replaced by an enzyme to obtain an enzymic hydrogel. Catalase was the first enzyme tested. Following the method set forth above, a gel was obtained but it rapidly redissolved during the washing steps. It is tought that this can be explained by the fact that catalase is composed of 4 subunits which were probably dissociated by the swelling force during the water uptake by the hydrogel. This example clearly demonstrates the unexpected important role of albumin protein in maintaining the integrity of the hydrogel structure. Consequently, albumin plays a key role as a co-protein of reticulation, avoiding the redissolution of the hydrogel. It was therefore found that an enzymatic gel would advantageously be prepared with both the enzyme and albumin protein in accordance with the method set forth above.

EXPERIMENTAL 100 mg of PEG dinitrophenyl carbonate of Mr 10,000 were mixed with 40 mg of BSA and 10 mg of acid phosphatase, catalase, peroxidase, lactase or glucose oxidase in 1.0 ml of borate buffer 0.1M pH 9.0 and allowed to polymerize in a test tube for 2 hours. The enzymatic hydrogels were then washed in accordance with the method set forth above and balanced in a buffer adequate for maintaining the enzyme activity. The different enzymatic hydrogels were pushed through a 700 μm mesh sieve and their respective activities were qualitatively evaluated in the presence of their respective substrates. The immobilization procedure was successful for all the enzymes immobilized in the PEG-albumin hydrogel. After 7 months of storage at 4° C. in a buffer solution, all the enzymatic hydrogels had maintained their bead form and showed residual enzymatic activity.

A more detailed study on the use of these hydrogels as immobilization matrices for enzymes was conducted using acid phosphatase enzyme (potato source). 10 mg of the enzyme were mixed with 40 mg of BSA and 100 mg of PEG, Mr 10,000, in 1.0 ml of borate buffer, pH 8.8. After two hours of polymerization, the enzymatic hydrogel was processed as mentioned before and was balanced with a citrate buffer 50 mM, pH 5.7. When comparing with the soluble enzyme, the apparent Km of the immobilized acid phosphatase was slightly higher than the Km of the native enzyme using p-nitrophenyl phosphate as substrate and was proportional to the size of the beads as described in Table 4 below.

TABLE 4

Evaluation of the influence of the particle size on the apparent Km and the maximum velocity of the phosphatase acid immobilized in the BSA-PEG hydrogel. P-nitrophenylphosphate was used as the substrate.

| Kinetic parameters | soluble enzyme | Particles size | | |
|---|---|---|---|---|
| | | 210 μm | 300 μm | 700 μm |
| Km (mM) | 0.42 | 0.71 | 0.94 | 1.49 |
| Vmax (μm min$^{-1}$ mg$^{-1}$) | — | 11.2 | 13.2 | 9.0 |

The reaction was carried out in column containing a weighted amounts of immobilized acid phosphatase at room temperature. The flow rate of the p-nitrophenylphosphate (50 mM citrate pH 5.7 containing 0.02% of NaN$_3$O) in the column was 0.3 ml/min.

Also, apparent Km determined for beads of 300 μm prepared with PEG of molecular masses of 4,600, 8,000, 10,000 and 20,000 were found to be 2.32, 1.6, 1.83, 1.09 mM p-nitrophenylphosphate, respectively. The decrease in the apparent Km along with the increase of molecular masses of PEG should be explained by an increase of the porosity. As the result of the increase of the porosity, the diffusion constraints applied on the substrate and product in the hydrogel were found to decrease. Data concerning the yield of immobilisation and other characteristics of the enzymatic hydrogel for the acid phosphatase are given in Table 5 below.

TABLE 5

Characteristics of enzymatic hydrogels obtained from a mixture containing 100 mg/ml PEG (Mr = 10,000), 20 to 45 mg/ml BSA and 30 to 5 mg/ml of phosphatase acid in 0.1M borate buffer, pH 8.8. After the polymerization, hydrogels were crunched and washed with 50 mM of borate buffer pH 8.8 and then equilibrated with 50 mM citrate buffer pH 5.2. The size of the dry particles was sieved over a 300 μm net. Activity of the immobilized enzyme particles was carried out after lyophilisation under optimal conditions (p-npp 10 mM, pH 5.7, flow rate 0.5 ml/min.

| Parameters | | | | |
|---|---|---|---|---|
| Amount of PA added (U) | 15 | 30 | 60 | 90 |
| Total protein added (mg)[1] | 50 | 50 | 50 | 50 |
| Protein released (mg) | 1.35 | 1.50 | 1.85 | 3.05 |
| Coupling yield (%) | 97.3 | 97 | 96.3 | 93.9 |
| PEG released (mg) | 30.3 | 30.5 | 35.7 | 35.5 |
| Immobilized PA (U) | 2.33 | 5.2 | 8.1 | 8.5 |
| Specific activity immobilized (mU/mg) | 48 | 107 | 168 | 181 |
| Immobilization yield (%) | 16 | 18 | 14 | 10 |

[1]including BSA and PA (2 U/mg) for a total amount of 50 mg of proteins.

Figure 6:
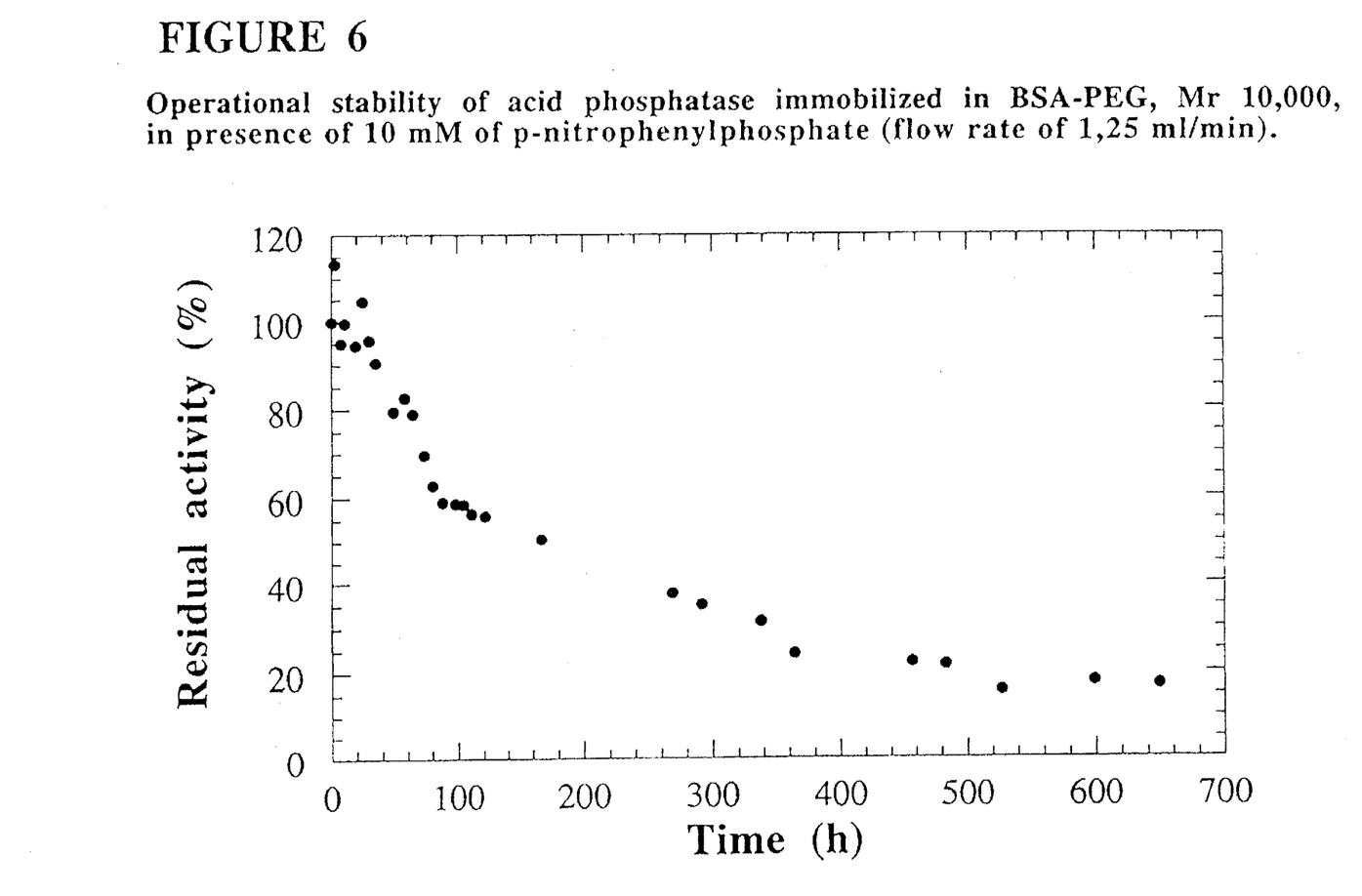
FIG. 6 shows the operational stability, expressed in percentage of residual activity (vertical scale) over time (horizontal scale) for acid phosphatase immobilized in BSA-PEG, Mr 10,000, in the presence of 10 mM of p-nitrophenylphosphate (flow rate of 1.25 ml/min).

Referring now to FIG. 6, when the enzymatic hydrogel was conserved at room temperature (20° C.) in a column, and used daily for a two to three hours period in optimal activity conditions (i.e. substrate p-nitrophenylphosphate (p-npp) at saturating level (10 mM) in 50 mM citrate buffer pH 5.7 containing sodium azide at 0.02%), the acid phosphatase hydrogel had a half-live of 169 h. This half-life is to be compared to a value of 150 hours obtained when the bioreactor was continuously operated in presence of 2 mM p-npp at 37° C. This data favorably compares with other data obtained with the same enzyme immobilized in a polyacrylamide matrix [Cantarella et al., *British Polymer J.*, 20 (6), 1988].

As another example of enzyme immobilization in hydrogels prepared with albumin and PEG 10,000 of Mr, the enzyme asparaginase of *E.coli* was used. The determination of the apparent Km for the substrate asparagine of the immobilized asparaginase in the hydrogel (slab thickness of 3 mm) was 2.4 μM of asparagine compared to 2.2 μM for the soluble form of the enzyme. The immobilization did not change the optimal pH of reaction which stayed at pH: 8.0. The operational stability of the immobilized enzyme in presence of a continuous feeding in substrate extend at 37° C. over a 20 days period without significant loss of activity.

Although the invention has been described above with respect with one specific form, it will be evident to a person skilled in the art that it may be modified and refined in various ways. It is therefore wished to have it understood that the present invention should not be limited in scope, except by the terms of the following claims.

What is claimed is:

1. A polymerized, hydrophilic, water-swellable, and water insoluble hydrogel consisting essentially of a cross-linked mixture of an aqueous solution of activated bifunctionalized polyethylene oxide and protein albumin, wherein said activated bifunctional polyethylene oxide consists of a polyethylene derivative of formula (I):

$$X-O-(CH_2CH_2O)_n-X \qquad (I),$$

wherein X represents a functionalized group capable of reacting with an amino, an S—H, an OH or a COOH group in an aqueous solution, said functionalized group not requiring a catalyst or activator to react with said amino, S—H, OH or COOH group, and n is from 45 to 800.

2. The hydrogel of claim 1, wherein said polyethylene oxide is an activated form of polyethylene glycol.

3. The hydrogel of claim 1, wherein said protein albumin is selected from the group consisting of bovine serum albumin, lactalbumin and ovalbumin.

4. The hydrogel of claim 2, wherein said protein albumin is selected from the group consisting of bovine serum albumin, lactalbumin and ovalbumin.

5. A polymerized, hydrophilic, water-swellable, and water insoluble hydrogel consisting essentially of a cross-linked mixture of an aqueous solution of activated bifunctionalized polyethylene oxide and protein albumin, wherein said activated bifunctional polyethylene oxide consists of a polyethylene derivative of formula (I):

X—O—(CH$_2$CH$_2$O)$_n$—X      (I), wherein X represents a functionalized group capable of reacting with an amino, an S—H, an OH or a COOH group in an aqueous solution, said functionalized group not requiring a catalyst or activator to react with said amino, S—H, OH or COOH group, and n is from 45 to 800, and further wherein said mixture includes nonreactive polymers having a molecular mass greater than 100,000.

6. The hydrogel of claim 5, wherein said unreactive polymers are polyethylene glycol.

7. A contact lens device, wherein said contact lens device is a polymerized, hydrophilic, water-swellable, and water insoluble hydrogel consisting essentially of a cross-linked mixture of an aqueous solution of activated bifunctionalized polyethylene oxide and protein albumin, wherein said activated bifunctional polyethylene oxide consists of a polyethylene derivative of formula (I):

X—O—(CH$_2$CH$_2$O)$_n$—X      (I), wherein X represents a functionalized group capable of reacting with an amino, an S—H, an OH or a COOH group in an aqueous solution, said functionalized group not requiring a catalyst or activator to react with said amino, S—H, OH or COOH group, and n is from 45 to 800.

8. An ophthalmic device designed for use in an ophthalmic environment, wherein said ophthalmic device is a polymerized, hydrophilic, water-swellable, and water insoluble hydrogel consisting essentially of a cross-linked mixture of an aqueous solution of activated bifunctionalized polyethylene oxide and protein albumin, wherein said activated bifunctional polyethylene oxide consists of a polyethylene derivative of formula (I):

X—O—(CH$_2$CH$_2$O)$_n$—X      (I), wherein X represents a functionalized group capable of reacting with an amino, an S—H, an OH or a COOH group in an aqueous solution, said functionalized group not requiring a catalyst or activator to react with said amino, S—H, OH or COOH group, and n is from 45 to 800.

9. A method of administering a physiologically active compound to a mammal comprising the steps of:

(a) loading the hydrogel of claim 1 with a solution comprising a therapeutically effective amount of said physiologically active compound, so that a loaded hydrogel is obtained; and (b) administering said loaded hydrogel to said mammal.

10. The method of claim 9, further comprising a physiologically acceptable carrier.

11. The method of claim 9, wherein said loaded hydrogel is a drug releasing composition having a physiologically acceptable form that is suitable for oral, rectal, cutaneous patch or sub-cutaneous implant administration.

12. The method of claim 9, wherein said loaded hydrogel is a wound dressing.

13. The method of claim 9, wherein said loaded hydrogel is artificial skin.

14. A matrix for immobilizing cells or enzymes, wherein said matrix is a polymerized, hydrophilic, water-swellable, and water insoluble hydrogel consisting essentially of a cross-linked mixture of an aqueous solution of activated bifunctionalized polyethylene oxide and protein albumin, wherein said activated bifunctional polyethylene oxide consists of a polyethylene derivative of formula (I):

X—O—(CH$_2$CH$_2$O)$_n$—X      (I), wherein X represents a functionalized group capable of reacting with an amino, an S—H, an OH or a COOH group in an aqueous solution, said functionalized group not requiring a catalyst or activator to react with said amino, S—H, OH or COOH group, and n is from 45 to 800.

15. A process for preparing an albumin-based hydrogel comprising the steps of:

(a) mixing a protein albumin solution with an activated polyethylene glycol derivative of formula (I):

X—O—(CH$_2$CH$_2$O)$_n$—X      (I), wherein X represents a functionalized group capable of reacting with an amino, an S—H, an OH or a COOH group, and n is from 45 to 800; and (b) agitating the mixture of step (a) at a pH of about 7.8 to 10.3 until a hydrogel results from the cross-linking of said protein albumin with said polyethylene glycol derivative of formula (I).

16. The process of claim 15, wherein step (a) includes nonreactive polymers having a molecular mass greater than 100,000.

* * * * *